United States Patent
Miyagi et al.

(10) Patent No.: US 8,696,551 B2
(45) Date of Patent: Apr. 15, 2014

(54) FLEXIBLE ENDOSCOPE SUITABLE FOR MRI

(75) Inventors: Kunihiko Miyagi, Chiba (JP); Masayuki Misawa, Chiba (JP); Tohru Tani, Shiga (JP); Yoshimasa Kurumi, Shiga (JP); Shigeyuki Naka, Shiga (JP)

(73) Assignees: Machida Endoscope Co., Ltd., Chiba (JP); Shiga University of Medical Science, Shiga (JP)

( * ) Notice: Subject to any disclaimer, the term of this patent is extended or adjusted under 35 U.S.C. 154(b) by 555 days.

(21) Appl. No.: 12/528,402

(22) PCT Filed: Feb. 22, 2008

(86) PCT No.: PCT/JP2008/053021
§ 371 (c)(1),
(2), (4) Date: Oct. 29, 2009

(87) PCT Pub. No.: WO2008/105328
PCT Pub. Date: Sep. 4, 2008

(65) Prior Publication Data
US 2010/0249511 A1    Sep. 30, 2010

(30) Foreign Application Priority Data
Feb. 26, 2007    (JP) .................................. 2007-046069

(51) Int. Cl.
*A61B 1/00*    (2006.01)
(52) U.S. Cl.
USPC .......................................... 600/140; 600/139
(58) Field of Classification Search
USPC ........................................................ 600/140
See application file for complete search history.

(56) References Cited

U.S. PATENT DOCUMENTS

| 3,670,721 A | 6/1972 | Fukami et al. |
| 4,024,858 A | 5/1977 | Chikama |

(Continued)

FOREIGN PATENT DOCUMENTS

| EP | 0430542 A2 | 11/1990 |
| EP | 0430542 A2 | 6/1991 |

(Continued)

OTHER PUBLICATIONS

Extended European Search Report issued by the European Patent Office in corresponding European Patent Application No. 08711795.8 dated May 16, 2011 (9 pages).

(Continued)

*Primary Examiner* — Matthew J Kasztejna
(74) *Attorney, Agent, or Firm* — Brian B. Shaw, Esq.; Thomas B. Ryan; Harter Secrest & Emery LLP

(57) ABSTRACT

The flexible endoscope 20 has a flexible insertion portion 22 to be inserted in an observation zone 11 of a MRI apparatus 10. The insertion portion 22 has an inner tube 71 made of resin, triple helical tubes 72 covering the inner tube 71 and an outer tube 73 made of resin and covering the triple helical tubes 72. The triple helical tubes 72 include a first helical band 721 helically wound around an outer peripheral surface of the inner tube 71, a second helical band 722 helically wound around an outer periphery of the first helical band 721 in a direction opposite to a winding direction of the first helical band 721 and a third helical band 723 helically wound around an outer periphery of the second helical band 722 in a direction opposite to the winding direction of the second helical band 722. The first to third helical bands 721, 722, 723 are made of phosphor bronze or copper-silver alloy, which are materials having low magnetic susceptibility.

3 Claims, 3 Drawing Sheets

(56) References Cited

U.S. PATENT DOCUMENTS

| | | | |
|---|---|---|---|
| 4,329,980 A | 5/1982 | Terada | |
| 4,677,818 A * | 7/1987 | Honda et al. | 57/224 |
| 4,805,595 A * | 2/1989 | Kanbara | 600/140 |
| 4,869,238 A * | 9/1989 | Opie et al. | 600/109 |
| 5,035,231 A | 7/1991 | Kubokawa et al. | |
| 5,046,351 A | 9/1991 | Takahashi et al. | |
| 5,058,567 A * | 10/1991 | Takahashi et al. | 600/139 |
| 5,402,788 A * | 4/1995 | Fujio et al. | 600/423 |
| 5,482,029 A | 1/1996 | Sekiguchi et al. | |
| 5,531,664 A * | 7/1996 | Adachi et al. | 600/149 |
| 5,752,912 A | 5/1998 | Takahashi et al. | |
| 5,788,714 A * | 8/1998 | Ouchi | 600/140 |
| 5,873,866 A * | 2/1999 | Kondo et al. | 604/526 |
| 6,444,358 B1 | 9/2002 | Allred, III et al. | |
| 6,520,214 B1 * | 2/2003 | Sugiyama et al. | 138/119 |
| 7,588,570 B2 * | 9/2009 | Wakikaido et al. | 606/52 |
| 2004/0080613 A1 | 4/2004 | Moriyama | |
| 2005/0059860 A1 | 3/2005 | Matsumoto et al. | |
| 2008/0208003 A1 | 8/2008 | Miyaga et al. | |

FOREIGN PATENT DOCUMENTS

| | | | |
|---|---|---|---|
| EP | 1961368 A2 | 2/2008 | |
| EP | 1961368 A2 | 8/2008 | |
| JP | S61-046923 A | 3/1986 | |
| JP | S62-053495 A | 3/1987 | |
| JP | H05-020702 | 3/1993 | |
| JP | H06-070879 | 3/1994 | |
| JP | H06-277174 A | 10/1994 | |
| JP | H09-238892 A | 9/1997 | |
| JP | H10-043125 A | 2/1998 | |
| JP | H10-305014 A | 11/1998 | |
| JP | H11-089795 A | 4/1999 | |
| JP | H11-0285533 A | 10/1999 | |
| JP | 2001-104239 | 4/2001 | |
| JP | 2002-125910 A | 5/2002 | |
| JP | 2006-061205 A | 3/2006 | |
| JP | 2008206699 A | 9/2008 | |

OTHER PUBLICATIONS

International Search Report for WO 2008/105328.

JP Office Action for Patent Application No. 2007-046066 mailed on Jan. 10, 2012.

US Office Action for U.S. Appl. No. 12/037,741 mailed on Oct. 15, 2009.

Extended European Search Report for EP Application 08250639.5 dated Jun. 25, 2010.

* cited by examiner

FLEXIBLE ENDOSCOPE SUITABLE FOR MRI

TECHNICAL FIELD

This invention relates to a flexible endoscope suitable for use with a MRI (Magnetic Resonance Imaging) apparatus, and particularly relates to a flexible tube in an insertion portion of the flexible endoscope.

BACKGROUND ART

As is well known, a MRI apparatus is used to obtain tomographic images of living bodies such as human bodies by magnetic nuclear resonance. An endoscope is inserted in a living body to observe inside the living body. An operation or a treatment can be performed through the endoscope. Many of metallic parts of an endoscope are generally made of stainless steel. This makes the endoscope not suitable for use with MRI because stainless steel affects magnetic fields.

One example of a possible solution is disclosed in Patent Document 1, in which low magnetic susceptibility metals such as brass are used for metallic parts of an endoscope in order to make the endoscope suitable for use in the vicinity of a MRI apparatus.

Patent Document 1: Japanese Published Patent Application No. 1110-305014

DISCLOSURE OF THE INVENTION

Problem to be Solved by the Invention

In recent years, there is a demand in the medical field for an endoscope that allows an operation or treatment to be performed endoscopically while an observation is being made with MRI. One way to meet this demand may be to make parts of an endoscope out of materials that affect magnetic field of a MRI apparatus as little as possible, as in the endoscope disclosed in Patent Document 1 mentioned above. However, it may reduce strengths of the endoscope, such as tensile strength, compressive strength and torsional strength, making the endoscope unsuitable for operation inside a living body, thus rendering the endoscope useless.

An alternative may be a rigid endoscope for which flexibility is not required. It may be relatively easy to make a rigid endoscope out of materials that satisfies strength requirements mentioned above and yet does not affect magnetic fields. However, a flexible endoscope needs to be freely bendable and at the same time to possess strength to maintain cross-sectional shape (cross-section is not deformed) even when curved to the maximum degree in addition to the strengths mentioned above. Moreover, to reduce burden on patient, the endoscope should be as small as possible in diameter.

It is an objective of the present invention to provide a flexible endoscope that meets basic requirements as mentioned above and, at the same time, is suitable for use with a MRI apparatus.

Means for Solving the Problem

In order to achieve the objective mentioned above, the present invention provides a flexible endoscope having a flexible insertion portion to be inserted in an observation zone of a MRI apparatus, characterized in that the insertion portion includes an inner tube made of resin, triple helical tubes covering the inner tube and an outer tube made of resin and covering the triple helical tubes; and that the triple helical tubes include a first helical band made of a low magnetic susceptibility material and helically wound around an outer periphery of the inner tube, a second helical band made of a low magnetic susceptibility material and helically wound around an outer periphery of the first helical band in a direction opposite to the winding direction of the first helical band, and a third helical band made of a low magnetic susceptibility material and helically wound around an outer periphery of the second helical band in a direction opposite to the winding direction of the second helical band.

Preferably, the low magnetic susceptibility materials for making the first to third helical bands have elasticity that allow the helical bands to expand and contract and to bend when being helically wound.

The low magnetic susceptibility materials (low magnetic permeability materials) mean materials whose magnetic susceptibility (magnetic permeability) are so low that they can hardly affect magnetic fields of MRI apparatus or materials whose magnetic susceptibility is substantially 0H/m. Specifically, magnetic susceptibility of substantially 0H/m means magnetic susceptibility (H/m) in the order of $1 \times 10^{-6}$ or less. The helical bands may be made of diamagnetic materials or paramagnetic materials.

Preferably, the low magnetic susceptibility material is phosphor bronze or copper-silver alloy. Phosphor bronze and cupper-silver alloy affect the magnetic fields of the MRI apparatus substantially less than nonmagnetic stainless steel, etc. Phosphor bronze and cupper-silver alloy are less expensive than titanium and have sufficient elasticity and tensile strength.

Examples of resins suitable for forming the inner tube include preferably polyolefin resins such as polypropylene and polyethylene. Polyamide resins such as nylon are also acceptable.

Examples of resins suitable for forming the outer tube include polyolefin resins such as polypropylene and polyethylene and polyamide resins such as nylon.

Preferably, a wire for bending a bendable portion in a distal end portion of the insertion portion is received in the inner tube; and the wire includes a string and adhesive, the string made by braiding a plurality of resin fibers, the adhesive impregnated and hardened in the string. Impregnation and hardening of the adhesive provides the string with adequate hardness and tension. This prevents the string from being elongated deformed even when tensile force is applied to the string during the bending operation.

Various known means of braiding, weaving and twisting, etc. may be adopted for the braiding.

Preferably, the adhesive is impregnated and hardened with a predetermined tensile force applied to the string. In this way, the wire can be homogenized in thickness. The tensile force is preferably slightly greater than a load applied to the wire during the bending operation of the bendable portion.

The string preferably includes a main portion received in the flexible insertion portion and a distal end portion passed through joint rings of the bendable portion, which are arranged in a line. Preferably, the adhesive is not impregnated in the distal end portion or is impregnated in the distal end portion to a less degree than in the main portion.

This prevents the string from being excessively hard in the bendable portion, thus facilitating smooth bending of the bendable portion.

Here, the degree of impregnation means the amount of adhesive impregnated in a unit length of the string.

Effect of the Invention

The present invention provides a flexible endoscope that has a required strength and flexibility and a small enough diameter and that can be used with a MRI apparatus.

DESCRIPTION OF THE REFERENCE NUMERALS

Figure 1:
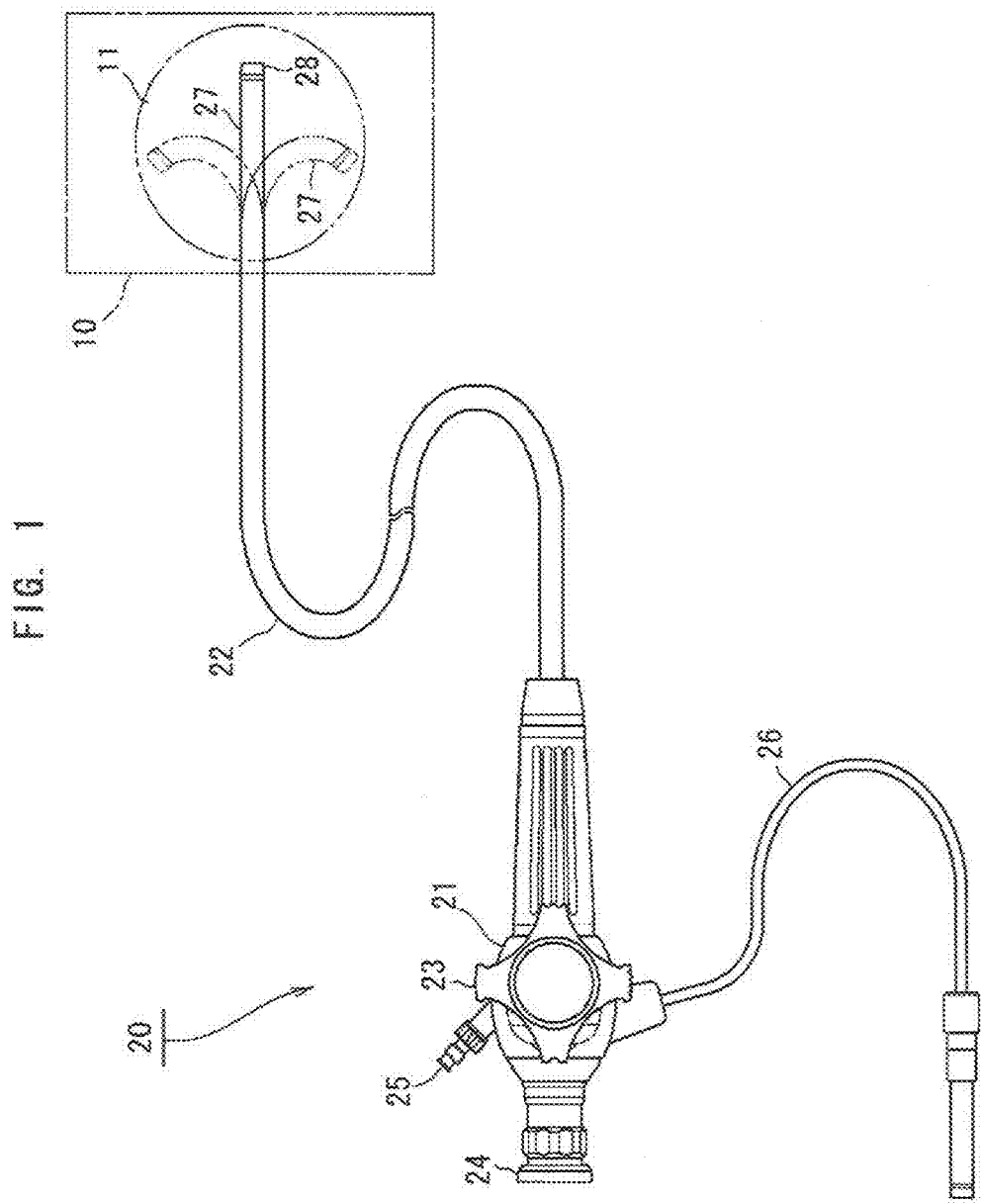
FIG. 1 is a side view of a flexible endoscope suitable for use with a MRI apparatus, showing an entire structure of the flexible endoscope according to one embodiment of the present invention.

MRI (Magnetic Resonance Imaging) apparatus
11 observation zone
20 endoscope
21 endoscope body
22 insertion portion
23 operation knob
24 ocular lens
25 forceps introduction portion
26 light guide
27 bendable portion
28 distal piece
29 joint ring
30 image guide
31 objective lens
40 working channel tube
41 mesh tube
50 bending operation wire (operation wire)
51 string
52 adhesive
53 bending operation wire guide (wire guide)
61, 62 securing piece
70 flexible tube (insertion portion body)
71 inner tube
72 triple helical tubes
721 first helical band
722 second helical band
723 third helical band
73 outer tube

BEST MODE FOR CARRYING OUT THE INVENTION

A preferred embodiment of the present invention will now be described.

In FIG. 1, reference numeral 10 refers to a MRI (Magnetic Resonance Imaging) apparatus and reference numeral 20 refers to an endoscope to be inserted in an observation zone 11 of the MRI apparatus 10 when to be used. The endoscope 20 includes an endoscope body 21 and an insertion portion 22. The endoscope body 21 has an operation knob 23 disposed in a side portion thereof, an ocular portion 24 disposed in a basal end portion thereof and a forceps introduction portion 25 disposed in an upper side portion thereof. A light guide 26 is drawn from a lower side portion of the endoscope body 21 and connected to a light source which is not shown. The insertion portion 22 extends from a distal end portion of the endoscope body 21. The insertion portion 22 is to be inserted in the observation zone 11.

Figure 3:
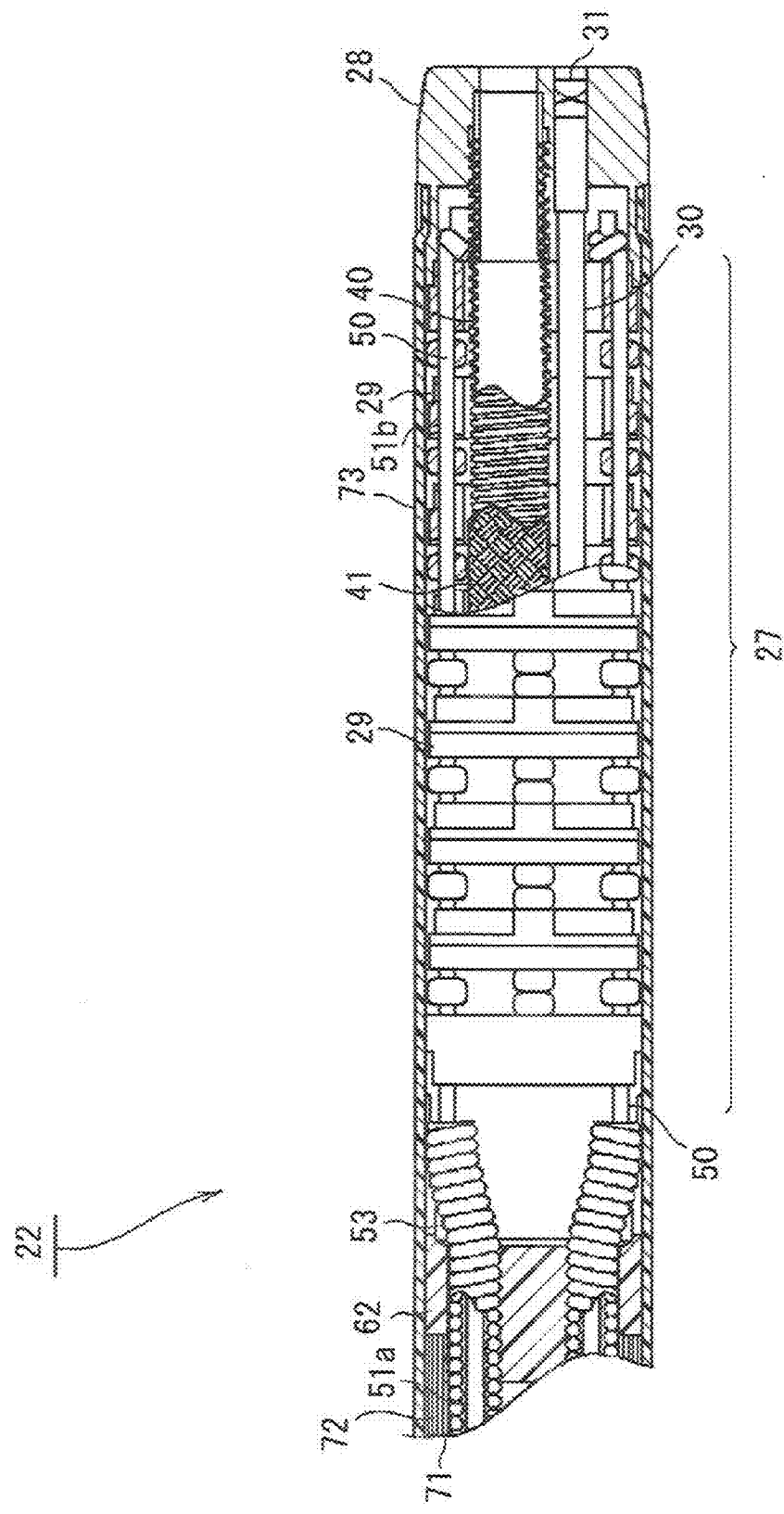
FIG. 3 is a side view showing an inner structure of a distal end portion (a bendable portion and a distal piece) of the insertion portion.

As shown in FIGS. 1 and 3, the insertion portion 22 is flexible and tubular. The insertion portion 22 has a bendable portion 27 in a distal end portion thereof and a distal piece 28 in a distal end side of the bendable portion 27.

As shown in FIG. 3, a plurality of joint rings 29 are disposed in the bendable portion 27. The joint rings 29 are made of low magnetic susceptibility materials (nonmagnetic materials, low magnetic permeability materials) such as brass. The joint rings 29 are arranged in a line, through which a distal end portion 51b of a bending operation wire (operation wire) 50 is passed. The bendable portion 27 as a whole can be bent by operating the operation knob 23 to operate the bending operation wire 50 (see the chain double-dashed line in FIG. 1).

Although the bendable portion 27 shown in the drawings can be bent in two directions, the bendable portion 27 may be bendable in one direction only or may be bendable in four directions.

The distal piece 28 is made of low magnetic susceptibility materials (nonmagnetic materials, low magnetic permeability materials) such as brass. Surfaces of the distal piece 28 are plated with gold, which is a low magnetic susceptibility material (nonmagnetic material, low magnetic permeability material).

The light guide 26, an image guide 30, a working channel tube 40 and the bending operation wire 50 are received inside the insertion portion 22 (including the bendable portion 27 and the distal piece 28).

The light guide 26 and the image guide 30 are composed of bundles of optical fibers, which are nonmagnetic materials. Although not shown in the drawings, a distal end of the light guide 26 reaches a distal end surface of the distal piece 28. Illumination light from the light source is transmitted along the light guide 26 and emitted therefrom to illuminate objects of observation.

An objective lens 31 is disposed at a distal end of the image guide 30. The objective lens 31 is made of optical glass or plastic, which are nonmagnetic materials. The objective lens 31 faces the distal end surface of the distal piece 28. Images of the objects of observation are transmitted through the objective lens 31 along the image guide 30 and can be observed through the ocular lens 24.

The working channel tube 40 is made of resin such as Teflon™, which is a nonmagnetic material, and is pleated like an accordion to provide flexibility. A distal end portion of the working channel tube 40 reaches the distal end surface of the distal piece 28. A Surgical instrument such as forceps is to be inserted through the forceps introduction portion 25 into the working channel tube 40. The surgical instrument is protruded from the distal end surface of the distal piece 28 so that it can be used for surgery. An outer peripheral surface of the working channel tube 40 is covered with a mesh tube 41 for restraining elongation. The mesh tube 41 is made of resin such as Nyron™, which is a nonmagnetic material.

Figure 2:
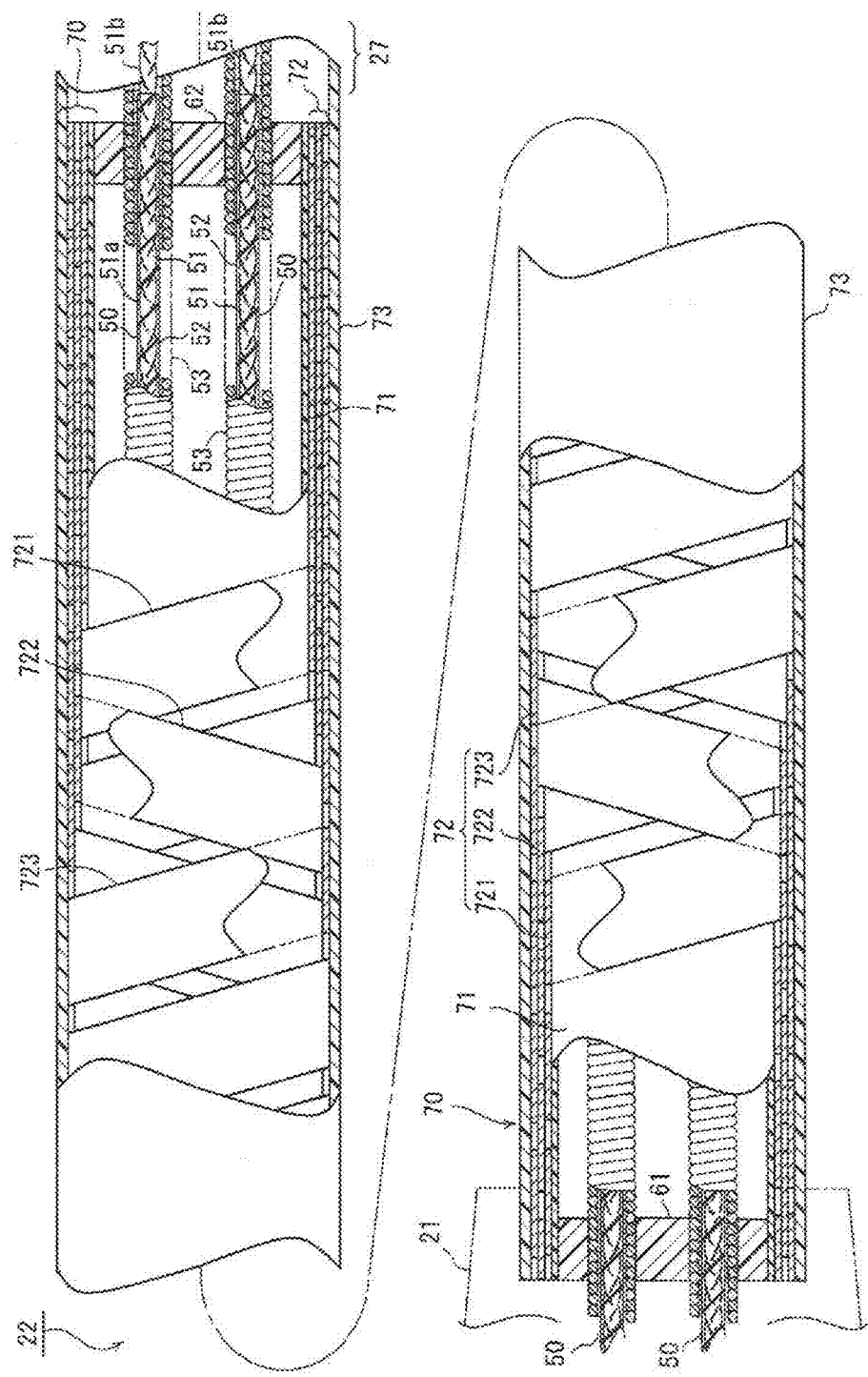
FIG. 2 is a side view showing an inner structure of a flexible portion of an insertion portion of the flexible endoscope.

As shown in FIGS. 2 and 3, a bending operation wire guide 53 (wire guide) is received in a flexible portion of the insertion portion 22 other than the bendable portion 27 and the distal piece 28. The bending operation wire guide 53 receives a main portion 51a of the bending operation wire 50 therein. The bending operation wire guide 53 is made of a material that has a required elasticity and low magnetic susceptibility (nonmagnetic materials, low magnetic permeability materials) into a coiled configuration. In this embodiment, copper-silver alloy is used as an example material for the bending operation wire guide 53. Phosphor bronze may be used instead of the copper-silver alloy. A distal end portion and a basal end portion of the bending operation wire guide 53 are secured to a peripheral wall of the insertion portion 22 via securing pieces 61, 62. The securing pieces 61, 62 are made of resin which is a nonmagnetic material.

As shown in FIG. 2, a flexible tube 70 constituting the peripheral wall (body) of the insertion portion 22 includes an inner tube 71, triple helical tubes 72 and an outer tube 73. Parts including the image guide 30, the light guide 26, the working channel tube 40, the bending operation wire guide 53 and the bending operation wire 50 are received inside the inner tube 71.

The inner tube 71 is made of resin which is a nonmagnetic material. Preferably, the resin forming the inner tube 71 has flexibility and also has sufficient tensile strength and compressive strength. Examples of the preferable resin include olefin resins such as polyethylene and polypropylene. In this embodiment, polyethylene (Irrax™ by Sumitomo Electric Industries), as an example, is used to form the inner tube 71.

Outer side of the inner tube 71 is covered with the triple helical tubes 72. The triple helical tubes 72 are composed of a first helical band 721, a second helical band 722 and a third helical hand 723. Each of the first to third helical bands 721, 722, 723 is composed of a helical band. The first helical band 721 is closely wound around an outer peripheral surface of the inner tube 71. The second helical band 722 is closely wound around an outer peripheral surface of the first helical band 721. A direction of winding of the second helical band 722 is opposite to that of the first helical band 721. The third helical band 723 is closely wound around an outer peripheral surface of the second helical band 722. A direction of winding of the third helical band 723 is opposite to that of the second helical band 722 and same as that of the first helical band 721. Opposite end portions of the triple helical tubes 72 are respectively fixed between the securing pieces 61, 62 and the outer tube 73.

The first to third helical bands 721, 722, 723 are made of a material that has a required elasticity, tensile strength and low magnetic susceptibility (nonmagnetic material, low magnetic permeability material). In this embodiment, phosphor bronze is used to make the first to third helical bands 721, 722, 723. Copper-silver alloy may be used instead of the phosphor bronze. The phosphor bronze and the copper-silver alloy sufficiently meet the requirements mentioned above.

The outer tube 73 is made of resin such as polypropylene and polyethylene, which are nonmagnetic materials. An external diameter of the outer tube 73 is 10 mm or smaller, and may be approximately 7 mm, for example. The outer tube 73 covers not only the flexible portion of the insertion portion 22 but also the bendable portion 27 and reaches the distal piece 28.

Detailed description of the bending operation wire 50 is provided below.

The bending operation wire 50 includes a string 51 made by braiding resin fibers which are nonmagnetic materials. The bending operation wire 50 is made by impregnating and hardening adhesive 52 which is a nonmagnetic material in the string 51. Olefin resin, such as polypropylene and polyethylene for example, is used as a material for the resin fibers to be made into the string 51 in this embodiment. Various methods of braiding can be employed, including various methods of knitting, weaving and twisting.

Various adhesive 52 can be employed for impregnating the string 51. Examples of suitable adhesive include commercially available products such as Cyanobond™.

The string 51 is pulled while being impregnated. Preferably, the string is pulled with a tensile force slightly greater than a load applied to the bending operation wire 50 when the bendable portion 27 is bent (approximately 2 kgf).

Example procedures for the impregnation include: suspending a weight having a weight corresponding to the load mentioned above by tying the weight at one end portion of the string 51; and dropping the adhesive 52 from an upper end portion of the string 51. The adhesive 52 is absorbed in mesh openings of the string 51, and impregnated in the string 51. Preferably, the tensile force is continuously applied to the string 51 until the adhesive 52 is hardened.

The impregnation and the hardening of the adhesive 52 provide the string 51 with appropriate hardness and tension.

The adhesive 52 is impregnated in the string 51, other than the distal end portion 51*b* thereof received in the bendable portion 27. In other words, the adhesive is impregnated in a portion of the string 51 received in the endoscope body 21 and the main portion 51*a* of the string 51 received in the inner tube 71 (flexible portion of the insertion portion 22).

The adhesive 52 is not impregnated in the distal end portion 51*b* of the string received in the bendable portion 27.

In the flexible endoscope 20, since the parts of the insertion portion 22 are made of nonmagnetic materials, placement of the insertion portion 22 in the vicinity of observation zone 11 of the MR1 apparatus does not substantially affect the magnetic field of the MRI apparatus. Thus interference on observation with the MRI can be limited or eliminated. This enables an operator to perform a surgery, etc. using the flexible endoscope 20 while observing the site with MRI.

Tensile strength, compressive strength, torsional strength and other kinds of strength required for the insertion portion 22 can be provided by the inner tube 71 and the triple helical tubes 72. Particularly, the inner tube 71 can provide the tensile strength and the compressive strength and the triple helical tubes 72 can provide the torsional strength. Moreover, when the flexible insertion portion 22 is bent at a certain point, a cross-sectional shape of the inner tube 71 at the certain point can be maintained by the triple helical tubes 72. Thus the inner tube 71 can be prevented from having the cross-section thereof deformed even when it is bent. Moreover, curvature of the insertion portion 22 can be limited by the triple helical tubes 72 to prevent the insertion portion 22 from being bent to an excessive degree.

Since the inner tube 71 can be reinforced by the triple helical tubes 72 as mentioned above, the outer diameter of the inner tube 71 can be reduced as much as possible and a thickness of a tube wall of the inner tube 71 can be reduced as much as possible. This serves to reduce the diameter of the insertion portion 22 as much as possible, thus reducing burden on patients.

Since the bending operation wire 50 includes the string 51 made of resin fibers, the bending operation wire 50 can be less expensive than those made of a metal wire, such as a stainless steel wire. The impregnation and hardening of the adhesive 52 in the string 51 can serve to prevent the bendable wire 50 made of resin from being elongated even when tensile force is applied thereto during the bending operation of the bendable portion 27.

Pulling the string 51 during the impregnation and hardening of the adhesive 52 can serve to homogenize the thickness of the bending operation wire 50.

Since the adhesive 52 is not impregnated in the distal end portion 51*b* of the string in the bendable portion 27, the bendable portion 27 can be bent easily.

The present invention is not limited to the embodiment described above, and various modifications can be made without departing from the spirit of the present invention.

For example, the parts mentioned above can be made of any other materials than those mentioned in the above embodiment as long as they have the low magnetic susceptibility (low magnetic permeability) and other required properties.

Other polyolefin resins such as polypropylene, polyamide resins such as nylon or any other resins can be used instead of polyethylene as a resin material for the inner tube 71.

Resins such as polypropylene or polyethylene may be used instead of the non-magnetic metals (alloys) such as phosphor bronze or copper-silver alloy to form the first to third helical bands 721, 722, 723.

Resins such as polypropylene or polyethylene may be used instead of the non-magnetic metals (alloys) such as copper-silver alloy or phosphor bronze to form the bending operation wire guide 53.

Polyamide resins such as nylon may be used instead of the polyolefin resins such as polypropylene or polyethylene as the resin fibers to form the string 51 of the bending operation wire 50.

The adhesive 52 may be impregnated in the string 51 by other methods than those disclosed in the above embodiment.

The tensile force applied to the string 51 during the impregnation and hardening of the adhesive 52 does not have to be slightly greater than the load applied to the bending operation wire 50 during the bending operation of the bendable portion 27. The tensile force may be generally equal to or considerably greater than the load mentioned above. Alternatively, the tensile force may be smaller than the load mentioned above, and the string 51 does not have to be pulled during the impregnation of the adhesive 52.

The adhesive 52 may also be impregnated in the distal end portion 51*b* of the string in the bendable portion 27. The degree of impregnation of the adhesive 52 may be smaller in the distal end portion 51*b* of the string than in the main portion 51*a*.

Industrial Applicability

The present invention may be applied to an endoscope for use with a MRI apparatus.

The invention claimed is:

1. A flexible endoscope suitable for a MRI apparatus, the endoscope comprising:
a flexible insertion portion to be inserted in an observation zone of the MRI apparatus, the insertion portion comprises a flexible tube constituting of the peripheral wall of the insertion portion, the flexible tube includes:
an inner tube made of resin;
triple helical tubes covering the inner tube, the triple helical tubes comprise:
a first helical band made of a low magnetic susceptibility material and helically wound around an outer periphery of the inner tube;
a second helical band made of a low magnetic susceptibility material and helically wound around an outer periphery of the first helical band in a direction opposite to the winding direction of the first helical band; and
a third helical band made of a low magnetic susceptibility material and helically wound around an outer periphery of the second helical band in a direction opposite to the winding direction of the second helical band; and
an outer tube made of resin and covering the triple helical tubes,
wherein the insertion portion, including each of the inner tube, the triple helical tubes, and the outer tube, has low magnetic susceptibility or non-magnetism and
wherein the insertion portion has a bendable portion in a distal end portion thereof, a wire for bending the bendable portion is received in the inner tube; and the wire comprises a string made by braiding a plurality of resin fibers; and adhesive impregnated and hardened in the string.

2. The endoscope according to claim 1 wherein the low magnetic susceptibility material to form one of the first to third helical bands is phosphor bronze or copper-silver alloy.

3. The endoscope according to claim 1 wherein the adhesive is impregnated and hardened with a predetermined tensile force applied to the string.

* * * * *